United States Patent [19]
Willcox et al.

[11] Patent Number: 5,863,544
[45] Date of Patent: Jan. 26, 1999

[54] COSMETIC/DERMATOLOGICAL W/O EMULSIONS HIGHLY CONCENTRATED IN HYDROXY ACIDS

[75] Inventors: Nathalie Willcox, Le Rouret; Agnés Ferrandis, Mougins; Isabelle Preuilh; Josiane Allec, both of Antibes, all of France

[73] Assignee: Centre International de Recherches Dermatologiques Galderma, Valbonne, France

[21] Appl. No.: 572,509

[22] Filed: Dec. 14, 1995

[30] Foreign Application Priority Data

Dec. 15, 1994 [FR] France ................................... 94 15130

[51] Int. Cl.⁶ ..................................................... A61K 7/48
[52] U.S. Cl. .......................... 424/401; 424/78.02; 424/61; 424/701; 514/557; 514/844; 514/937
[58] Field of Search ................................ 424/401, 78.02, 424/61, 70.1; 514/557, 844, 937

[56] References Cited

U.S. PATENT DOCUMENTS 4,380,549  4/1983  Van Scott et al. ...................... 424/317
4,772,592  9/1988  Benzoni ..................................... 514/63

FOREIGN PATENT DOCUMENTS 0456459  11/1991  European Pat. Off. .

*Primary Examiner*—Jyothsna Venkat
*Attorney, Agent, or Firm*—Burns, Doane, Swecker & Mathis, L.L.P.

[57] ABSTRACT

Topically applicable cosmetic/dermatological compositions well suited for the therapeutic treatment or care of human skin, nails, hair and/or of the scalp, in particular for treating and/or preventing xerosis, ichthyosis, actinic keratosis and/or photoinduced cutaneous aging, comprise a water-in-oil emulsion containing (a) at least 10% by weight of at least one hydroxy acid, (b) an effective emulsifying amount of at least one polyoxyalkylenated silicone, and (c) an effective coemulsifying amount of at least one polyol alkyl ester, polyol alkyl ether or oxyalkylenated alkyl ether, with the proviso that the subject compositions are devoid of any $C_1$–$C_4$ alkanol.

14 Claims, No Drawings

COSMETIC/DERMATOLOGICAL W/O EMULSIONS HIGHLY CONCENTRATED IN HYDROXY ACIDS

BACKGROUND OF THE INVENTION

1. Technical Field of the Invention

The present invention relates to novel cosmetic/dermatological compositions for topical application, comprising water-in-oil emulsions containing a high content of hydroxy acids, for therapeutic treatment or care of the skin, nails or hair and/or of the scalp, and to the use of same, in particular for treating and/or preventing xerosis, ichthyosis, actinic keratosis and/or photoinduced cutaneous aging.

2. Description of the Prior Art

It is known to this art to employ hydroxy acids for preventing or reducing the dermatological signs of aging of the skin and/or of hair, which are due to factors that are intrinsic to aging or else to external factors, such as, especially, UV irradiation, air pollution, wind, cold, heat and cigarette smoke. These are also known active agents for treating dermatological afflictions related to a disorder of the keratinization of the skin, nails and/or hair, such as especially acne, xerosis, ichthyosis and actinic keratosis.

However, these hydroxy acids are difficult to formulate as an emulsion in cream or milk form. Indeed, when they are incorporated in a concentrated amount, the hydroxy acids render the formulation unstable and therefore difficult to commercially exploit.

In addition, these compounds present the disadvantage of causing tingling, itching or pulling sensations after their application, which can result in considerable discomfort. To avoid this discomfort, it has been considered to release the hydroxy acids slowly and gradually, while maintaining their effectiveness.

U.S. Pat. No. 4,772,592 describes a stable water-in-oil emulsion for topical application, for treating acne, which includes a $C_1$–$C_4$ alkyl lactate, a silicone oil, a nonionic liquid emulsifier and $C_1$–$C_4$ alkanol, these constituents being present in specific amounts. Volatile polar liquids such as the alkyl lactate and the alkanol are essential ingredients of this emulsion because, together with the silicone oil, they stabilize the emulsion. However, $C_1$–$C_4$ alkanols present the disadvantage of being irritants to the skin or to the mucosae and hence of contributing to the aforesaid discomfort caused by the hydroxy acids.

SUMMARY OF THE INVENTION

Accordingly, a major object of the present invention is the provision of novel cosmetic/dermatological emulsions having a high content of hydroxy acids but which are stable over time.

Another object of this invention is the provision of novel cosmetic/dermatological compositions containing hydroxy acids which do not cause discomfort, as described above, when topically applied to the skin or the mucosae.

Briefly, the present invention, features novel cosmetic/dermatological water-in-oil emulsions comprising:

(a) from 10% to 30% by weight of hydroxy acids, (b) from 1% to 15% by weight of at least one silicone bearing polyoxyalkylene substituents, and (c) from 0.1% to 6% by weight of at least one coemulsifying compound which comprises a polyol alkyl ester, a polyol alkyl ether or an alkyl ether bearing oxyalkylene substituents, with the proviso that said emulsions are devoid of any $C_1$–$C_4$ alkanol.

DETAILED DESCRIPTION OF BEST MODE AND SPECIFIC/PREFERRED EMBODIMENTS OF THE INVENTION

More particularly according to the present invention, despite the large quantity of hydroxy acids contained therein the subject compositions exhibit stability in storage. Thus, the compositions of this invention can be stable for at least three months at a temperature of 45° C.

Moreover, by virtue of the aforesaid specific formulation, the release of the active hydroxy acid is attained slowly and gradually when the composition is topically applied to the skin, nails, hair and/or the scalp, which makes it very pleasant for the ultimate user.

The hydroxy acids of the present invention applies may be α-hydroxy acids or β-hydroxy acids, which may be linear, branched or cyclic and saturated or unsaturated. The hydrogen atoms in the carbon chain may, in addition, be substituted by halogens or by halogenated, alkyl, acyl, acyloxy, alkoxycarbonyl or alkoxy radicals having from 2 to 18 carbon atoms. α- and β-keto acids may also be employed.

The hydroxy acids most widely employed in cosmetics or in dermatology are glycolic, lactic, malic, tartaric, citric, mandelic and salicylic acids and the alkylated derivatives thereof, such as 5-n-octanoyl-salicylic acid, 5-n-dodecanoylsalicylic acid or 2-hydroxy-3-methylbenzoic acid, or their alkoxylated derivatives such as 2-hydroxy-3-methoxy-benzoic acid. Lactic acid, glycolic acid and citric acid are the preferred hydroxy acids according to the invention.

It should be appreciated that the α- or β-hydroxy acid may comprise a mono- or polycarboxylic acid substituted by one or more hydroxyl functional groups, at least one of these hydroxyl functional groups being in the α- or β-position relative to the carboxylic acid functional group.

This acid may be incorporated into the compositions of the invention in the form of the free acid and/or in the form of one of the associated salts thereof (especially salts with an organic base or an alkali metal), in particular depending on the final Ph intended for the composition, or else in the form of one of its esters or of its corresponding amides, or optionally, in the form of the corresponding lactide (a form provided by autoesterification of the molecules).

The hydroxy acids are preferably in a free acid form.

It will of course be appreciated that the compositions in accordance with the invention may contain one or more hydroxy acids.

In the above description, and in that to follow, the amount of hydroxy acid employed is expressed as the percentage by weight of free acid, unless otherwise indicated.

The amount of hydroxy acid incorporated advantageously ranges from 12% to 28% by weight relative to the total weight of the composition.

The polyoxyalkylenated silicone is included in the compositions of the present invention, in particular, for its emulsifying power.

The polyoxyalkylenated silicones according to this invention advantageously have the structural formula (I):

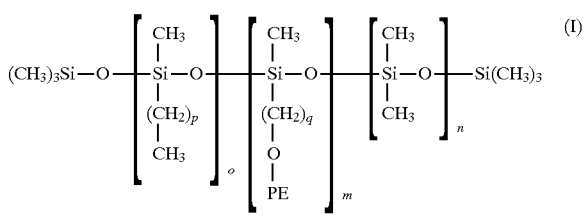

in which PE is a radical (—C$_2$H$_4$O)$_x$(—C$_3$H$_6$O)$_y$—R, wherein R is a hydrogen atom or an alkyl radical having from 1 to 4 carbon atoms, x is a number ranging from 10 to 100 and y is a number ranging from 0 to 80; m is a number ranging from 1 to 25; n is a number ranging from 10 to 200; o is a number ranging from 0 to 100; p is a number ranging from 7 to 17; and q is a number ranging from 0 to 4.

Preferably, a polyoxyalkylenated silicone having structural formula (I) is used, in which q is equal to 3, o ranges from 1 to 100, with the proviso that o is not less than m and that 3 o is less than n, and in which the molecular weight of PE ranges from 250 to 2,000 with x and y selected such that their weight ratio x/y ranges from 100/0 to 20/80.

A polyoxyalkylene-substituted silicone is advantageously employed, corresponding to the structural formula (I), in which m is equal to 5, n is equal to 75, o ranges from 20 to 25, p is equal to 15, q is equal to 3 and PE is completely polyoxyethylenated and has a molecular weight of 400. Thus, more particularly, the cetyl dimethicone copolyol marketed under the trademark name Abil EM 90® by Goldschmidt is employed.

The emulsions according to the invention preferably comprise from 1% to 5% by weight of at least one polyoxyalkylenated silicone.

The alkyl moiety of the coemulsifying compound employed in the present invention preferably has from 12 to 20 carbon atoms.

The coemulsifying oxyalkylene-substituted alkyl ether typically comprises from 2 to 10 oxyalkylene structural units per molecule of ether.

The coemulsifying oxyalkylenated alkyl ether is advantageously a fatty ether substituted by oxyalkylene, generally oxyethylene and/or oxypropylene structural units. It advantageously comprises a number of oxyalkylene units ranging from 2 to 4 per molecule of ether.

Among the oxyalkylenated fatty ethers according to the present invention, preferred is the ether of myristyl alcohol and of polypropylene glycol, such as Witconol APM® (3 moles of propylene oxide) marketed by Witco.

The coemulsifying polyol alkyl ester or polyol alkyl ether is advantageously a polyglycerolated fatty ester or fatty ether typically comprising from 2 to 10 glycerol units per molecule of ester or ether, or a fatty ester or a fatty ether derived from a sugar such as sorbitol, sorbitan or methylglucoside, or else a fatty ester or a fatty ether of glycerol and of a sugar such as sorbitol, sorbitan or methylglucoside.

The polyol alkyl esters or polyol alkyl ethers may be mono-, di- or polyesters or -ethers.

These coemulsifiers may be employed either alone or in admixture.

Among the polyol alkyl esters or polyol alkyl ethers, preferred is a polyglycerol isostearate such as Isolan Gl 34® marketed by Goldschmidt, sorbitan isostearate such as Arlacel 987® marketed by ICI, sorbitan glycerol isostearate such as Arlacel 986® marketed by ICI and methylglucose sesquistearate such as glycate IS® marketed by Amerchol.

The amount of coemulsifying compound comprising a polyol alkyl ester, polyol alkyl ether or oxyalkylenated alkyl ether in the compositions of the invention advantageously ranges from 0.1% to 3% by weight.

Ethanol, n-propanol, isopropanol and n-butanol are exemplary of the C$_1$–C$_4$ alkanols which are not included in the compositions/emulsions according to the invention.

The fatty phase of the subject emulsions may include saturated or unsaturated hydrocarbon compounds such as liquid petrolatum or perhydrosqualene, or aliphatic or aromatic fatty esters such as a C$_{12}$–C$_{15}$ alkyl benzoate, octyldodecanol or octyl stearate, or triglycerides such as the triglycerides of capric or caprylic acid or else polydimethylsiloxanes.

The proportion of the fatty phase advantageously ranges from 20% to 40% of the total weight of the composition according to the invention.

The fatty phase of the subject compositions preferably comprises at least one polydimethylsiloxane, the amount thereof in the composition generally ranging from 10% to 30% by weight.

It is thus intended to employ volatile polydimethylcyclosiloxanes which have a viscosity of less than 5 mm$^2$ s$^{-1}$, such as, especially, the cyclomethicone tetramer or pentamer marketed by Dow Corning (Dow Corning 344 Fluid and Dow Corning 345 Fluid) or else volatile hexamethyldisiloxane which has a viscosity of less than 0.65 mm$^2$s$^{-1}$, such as, especially, the Rhodorsil Oils marketed by Rhône-Poulenc (RP 70041VO65). At least one nonvolatile polydimethylsiloxane may also be employed, such as a polydimethylsiloxane which has a viscosity higher than 5 mm$^2$ s$^{-1}$, especially ranging from 50 to 1,000 mm$^2$s$^{-1}$, such as, for example, Dow Corning 200 Fluid.

These also may be employed alone, or, preferably, in admixture.

To enhance, optionally, the stability of the composition at low temperatures, or to prevent, also optionally, the recrystallization of certain hydroxy acids, or else, again optionally, to render the composition transparent, polyols such as glycerol, 1,2-propylene glycol and sorbitol may be added to the compositions in amounts which generally range from 0.5% to 15% by weight.

To enhance, optionally, the stability of the composition at higher temperatures, natural or synthetic waxes may be added thereto, such as beeswax, carnauba wax, butter tree butter or silicone waxes or lipid dispersions of modified hectorites or else aluminum or calcium stearate or electrolytes such as sodium chloride or magnesium sulfate.

The compositions/emulsions according to the invention may also include titanium dioxide microparticles having a mean diameter ranging from 1 to 100 nm, preferably from 10 to 40 nm. Two forms of titanium dioxide are available, one type which is dispersible in the aqueous phase and another type which is dispersible in the fatty phase.

The titanium dioxide particles of the type which is dispersible in the aqueous phase may be particles that are uncoated, or particles coated with a material providing them with a hydrophilic surface, such as aluminum oxide or aluminum silicate.

Titanium dioxide particles of the type which is dispersible in the fatty phase are particles coated with a material providing them with a lipophilic surface, such as aluminum stearate, aluminum laurate, zinc stearate or, optionally, siliceous, organic compounds.

The amount of titanium dioxide in the composition according to the present invention generally ranges from 0.5% to 2% by weight.

The compositions/emulsions according to the invention may, of course, additionally contain inert or even cosmetically or dermatologically active additives or adjuvants, or combinations thereof.

Enhancing agents, preservatives such as esters of para-hydroxybenzoic acid, stabilizing agents, moisture-regulating agents and pH-regulating agents may also be added.

The compositions according to the invention may, therefore, additionally comprise an active agent intended especially for the treatment or the prevention of cutaneous afflictions, including acne, mycosis, seborrhoeic dermatitis, eczema, rosacea, heliodermatosis and cutaneous aging, or scalp or nail maladies.

Exemplary of the dermatologically active agents are:

(1) agents modifying cutaneous differentiation and/or proliferation and/or pigmentation, such as compounds whose activity is mediated by the nuclear receptors of the superclass of the steroids/thyroidal hormones, in particular retinoic acid, its isomers and derivatives thereof, for example retinol or retinaldehyde, and similar synthetic compounds, vitamin D or derivatives thereof, estrogens, and antineoplastics such as 5-fluorouracil;

(2) antibiotics such as clindamycin phosphate, erythromycin or antibiotics of the tetracycline class;

(3) antibacterials, in particular benzoyl peroxide;

(4) anti-infectives, in particular metronidazole;

(5) antifungals, in particular the compounds of the imidazole class, polyene compounds such as amphotericin B or compounds of the allylamine class such as terbinafine;

(6) steroidal anti-inflammatory agents such as hydrocortisone, betamethasone valerate or clobetasol propionate, or nonsteroidal anti-inflammatory agents such as ibuprofen or diclofenac or salts thereof;

(7) antipuritics such as capsaicin or the NK1 inhibitors or lithium salts;

(8) analgesics;

(9) antivirals such as acyclovir;

(10) blockers of ion channels, such as minoxidil and derivatives thereof;

(11) free-radical antagonists such as alpha-tocopherol or esters thereof, dismutase superoxides or certain metal-chelating agents.

The concentration of these active agents in any particular composition depends, of course, on the nature of the active agent and intended therapeutic effect; it generally ranges from 0.001% to 10% by weight of the composition.

Advantageously, the compositions according to the invention do not include any compounds of a nature or in an amount such that they render the composition uncomfortable when it is topically applied to the skin or the mucosae.

The compositions according to the invention are typically in the form of a milk, cream, or of a transparent emulsion.

The compositions according to the invention may be formulated via any technique per se known to this art. Thus, the emulsifying agent or the emulsifying mixture may be dissolved or dispersed in the fatty phase. Water is added next, preferably slowly. Stirring may be carried out by any known means. It is preferable to stir such as to form a preemulsion. The other compounds of the emulsion may be simply added beforehand to the phase in which they are soluble or dispersible. The emulsion may be stabilized using a stirring system of the rotor-stator type, preferably at high speed.

The compositions according to the invention are particularly useful for topical application, for the therapeutic treatment or care of the skin, nails, hair and/or of the scalp, and preferably for treating and/or preventing xerosis, ichthyosis, actinic keratosis and/or photoinduced cutaneous aging.

In order to further illustrate the present invention and the advantages thereof, the following specific examples are given, it being understood that same are intended only as illustrative and in nowise limitative.

In said examples to follow, as in the above description, all parts and percentages are given by weight, unless otherwise indicated.

EXAMPLES

General technique for the formulation of the subject compositions

The emulsifying agent or emulsifying mixture was dissolved or dispersed in the fatty phase. Water was next added slowly. The stirring was moderate to provide a preemulsion. The other compounds of the emulsion were added beforehand to the phase in which they were soluble or dispersible. The emulsion was stabilized using a stirring system of the rotor/stator type, this being at high speed.

In the examples, the following abbreviations are employed:

POB=para-hydroxybenzoate,

PPG=polypropylene glycol,

POP=polyoxypropylene,

POE=polyoxyethylene.

Example 1

| Tradename/trademark | Chemical nomenclature | % |
|---|---|---|
| Formulation: | | |
| FATTY PHASE: | | |
| (a) Abil90 ® (Goldschmidt) | Cetyl dimethicone copolyol | 2.50 |
| (b) Witconol APM ® | PPG-3 myristyl ether | 0.50 |
| (c) Dow Corning 344 fluid ® | Cyclomethicone | 9.00 |
| (d) Dow Corning 345 fluid ® | Cyclomethicone | 9.00 |
| (e) Dow Corning 200 fluid ® | Dimethicone | 2.00 |
| (f) TiO$_2$ PW Covasil S ® | TiO$_2$ + alkylsilane + polymethyl methacrylate | 1.00 |
| AQUEOUS PHASE: | | |
| (a) Glycerol | | 3.00 |
| (b) 70% Sorbitol | | 5.00 |
| (c) Citric acid, 1H$_2$O | | 27.30 (25% anhydrous) |
| (d) Methyl POB | | 0.15 |
| (e) NaCl | | 0.60 |
| (f) 32% Aqueous ammonia | q.s. | pH 3 (#) |
| (g) Water | q.s. | 100 |

(#) i.e., 4.50% of 32% aqueous ammonia

This composition presented the advantage of being stable and of being well tolerated by human skin, despite the large amount of citric acid present therein (=25%).

Example 2

Formulation:

| Tradename/Trademark | Chemical nomenclature | % |
|---|---|---|
| FATTY PHASE: | | |
| (a) AbilEm90 ® (Goldschmidt) | Cetyl dimethicone copolyol | 2.50 |
| (b) Witconol APM ® | PPG-3 myristyl ether | 0.50 |
| (c) Dow Corning 344 fluid ® | Cyclomethicone | 9.00 |
| (d) Dow Corning 345 fluid ® | Cyclomethicone | 9.00 |
| (e) Dow Corning 200 fluid ® | Dimethicone | 2.00 |
| (f) TiO$_2$ PW Covasil S ® | TiO$_2$ + alkylsilane + polymethyl methacrylate | 1.00 |
| AQUEOUS PHASE: | | |
| (a) Citric acid, 1H$_2$O | | 27.30 (25% anhydrous) |
| (b) Methyl POB | | 0.15 |
| (c) NaCl | | 0.60 |
| (d) 32% Aqueous ammonia | q.s. | pH 3 (#) |
| (e) Water | q.s. | 100 |

(#) i.e., 4.50% of 32% aqueous ammonia

This composition was stable for 6 months at ambient temperature.

Example 3

Formulation:

| Tradename/Trademark | Chemical nomenclature | % |
|---|---|---|
| (a) Arlacel 780 ® (ICI) | POP-POE glycerol sorbitan hydroxyisostearate | 6 |
| (b) Thick petrolatum | | 10 |
| (c) Dow Corning 344 Fluid | Cyclomethicone | 15 |
| (d) Water | | 50.18 |
| (e) Piperazine | | 4.82 |
| (f) Lactic acid (90%) | | 12.00 |
| (g) Sodium chloride | | 2.00 |

After one month at a temperature of 45° C., the composition displayed a large exudate.

Example 4 (Comparative)

Formulation:

| Tradename/Trademark | Chemical nomenclature | % |
|---|---|---|
| (a) Arlacel 582 ® (ICI) | POE glycerol sorbitan isostearate | 1 |
| (b) Arlatone T ® (ICI) | POE(40)-sorbitol septaoleate | 4 |
| (c) Fluid liquid petrolatum | Mineral oil | 10 |
| (d) Rilanit G16S ® (Henkel) | Isocetyl stearate | 10 |
| (e) Propyl POB | | 0.05 |
| (f) Water | | 47.95 |
| (g) Methyl POB | | 0.10 |
| (h) Glycerine | Glycerol | 3 |
| (i) Lubragel CG ® (Sederma) | Polyglyceryl methacrylate and propylene glycol | 5 |
| (j) Glycolic acid | | 12 |
| (k) Sodium hydroxide | | 4.68 |
| (l) Sodium chloride | | 2.00 |

After one month at a temperature of 45° C., the composition displayed a large exudate.

Example 5 (Comparative)

Formulation:

| Tradename/Trademark | Chemical nomenclature | % |
|---|---|---|
| (a) AbilEM90 ® (Goldschmidt) | Cetyl dimethicone copolyol | 2.5 |
| (b) Eutanol G ® (Henkel) | Octyldodecanol | 9.5 |
| (c) Dow Corning 344 Fluid ® | Cyclomethicone | 15 |
| (d) Water | | 34.75 |
| (e) Methyl POB | | 0.15 |
| (f) Glycerine | Glycerol | 3.00 |
| (g) Lubragel CG ® (Sederma) | Polyglyceryl methacrylate and propylene glycol | 5.00 |
| (h) Anhydrous citric acid | | 25.00 |
| (i) 32% Aqueous ammonia | | 4.50 |
| (j) Sodium chloride | | 0.60 |

This composition, without any coemulsifying compound, exuded from the first month of stability.

Example 6 (Comparative)

Formulation:

| | Tradename/Trademark | Chemical nomenclature | % |
|---|---|---|---|
| (a) | Arlacel 60 ® (ICI) | Sorbitan monostearate | 4.5 |
| (b) | Amphisol K ® (Givaudan) | Potassium cetyl phosphate | 0.50 |
| (c) | Rilanit G16S ® (Henkel) | Isocetyl stearate | 4.00 |
| (d) | Stearyl alcohol | | 4.00 |
| (e) | Dow Corning 200 ® (350 cps) | Dimethicone | 0.50 |
| (f) | Propyl POB | | 0.05 |
| (g) | Fluid liquid petrolatum | Fluid mineral oil | 3.00 |
| (h) | Water | | 39.25 |
| (i) | Methyl POB | | 0.10 |
| (j) | Glycerine | Glycerol | 3.00 |
| (k) | Phenoxy ethanol | | 0.50 |
| (l) | Lubragel CG ® (Sederma) | Polyglyceryl methacrylate and propylene glycol | 5.00 |
| (m) | Anhydrous citric acid | | 25.00 |
| (n) | 32% Aqueous ammonia | | 8.80 |
| (o) | Methocel E4M Premium ® (Dow Chemical) | Hydroxypropyl methyl cellulose | 0.30 |
| (p) | Veegum HS ® (Vanderbilt) | Magnesium aluminum silicate | 1.50 |

This composition of oil-in-water emulsion type exhibited phase separation from the first day of stability.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition adopted for the therapeutic treatment or care of human skin, nails, hair or the scalp, comprising a water-in-oil emulsion containing (a) from 10% to 30% by weight of at least one hydroxy acid selected from the group consisting of glycolic, lactic, malic, tartaric, citric, mandelic, salicylic, 5-n-octanoylsalicylic acid, 5-n-dodecanoylsalicylic acid, 2-hydroxy-3-methylbenzoic acid, and 2-hydroxy-3-methoxybenzoic acid; (b) from 1 to 15% by weight of at least one polyoxyalkanylated silicone having the structural formula (I)

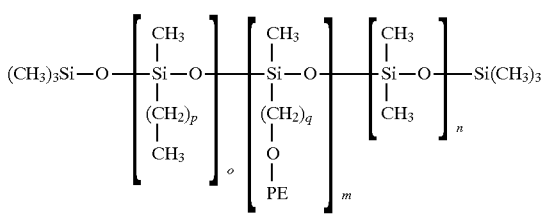

in which PE is a radical $(-C_2H_4O)_x(-C_3H_6O)_y-R$, wherein R is a hydrogen atom or an alkyl radical having from 1 to 4 carbon atoms, x is a number ranging from 10 to 100 and y is a number ranging from 0 to 80; m is a number ranging from 1 to 25; n is a number ranging from 10 to 200; o is a number ranging from 0 to 100; p is a number ranging from 7 to 17; and q is a number ranging from 0 to 4; and (c) an effective coemulsifying amount of at least one polyol alkyl ester, compound contained in an amount ranging from 0.1 to 6% by weight which is selected from the group consisting of polyglycerol isostearate, sorbitan isostearate, sorbitan glycerol isostearate, methylglucose sesquistearate, myristyl alcohol ether, polypropylene glycol ether, and with the proviso that said composition is devoid of any $C_1-C_4$ alkanol.

2. The cosmetic/dermatological composition as defined by claim 1, wherein said at least one hydroxy acid (a) is lactic acid, glycolic acid or citric acid.

3. The cosmetic/dermatological composition as defined by claim 1, comprising from 12% to 26% by weight of said at least one hydroxy acid (a).

4. The cosmetic/dermatological composition as defined by claim 1, the fatty phase of said emulsion comprising at least one compound selected from the group consisting of liquid petrolatum, perhydrosqualene, $C_{12}-C_{15}$ alkylbenzoate, octyldodecanol, octylstearate, and a triglyceride of capric or caprylic acid, and polydimethylsiloxane.

5. The cosmetic/dermatological composition as defined by claim 1, the fatty phase of said emulsion comprising from 20% to 40% of the total weight thereof.

6. The cosmetic/dermatological composition as defined by claim 1, the fatty phase of said emulsion comprising at least one polydimethylsiloxane.

7. The cosmetic/dermatological composition as defined by claim 1, further comprising from 0.5% to 15% by weight of a polyol.

8. The cosmetic/dermatological composition as defined by claim 1, further comprising a natural or synthetic wax, a silicone wax, a lipid dispersion of a modified hectorite, aluminum or calcium stearate, or an electrolyte.

9. The cosmetic/dermatological composition as defined by claim 1, further comprising titanium dioxide microparticles having a mean diameter ranging from 1 to 100 nm.

10. The cosmetic/dermatological composition as defined by claim 9, comprising from 0.5% to 2% by weight of said titanium dioxide microparticles.

11. The cosmetic/dermatological composition as defined by claim 1, further comprising a cosmetically or dermatologically active additive or adjuvant.

12. The cosmetic/dermatological composition as defined by claim 1, comprising a cream, milk or transparent emulsion.

13. A method for the therapeutic treatment or care of at least one the skin, nails, hair and scalp of a mammalian organism in need of such treatment/care, comprising topically administering thereto, for such period of time as to elicit the desired biological response, an effective amount of the cosmetic/dermatological composition as defined by claim 1.

14. The cosmetic/dermatological composition as defined by claim 1, which further comprises an active agent selected from the group consisting of active agent which modifies at least one of cutaneous differentiation, proliferation and pigmentation, an antibiotic, an antibacterial, an antiinfective, an antifungal, a steroidal anti-inflammatory, a nonsteroidal anti-inflammatory, an antipruritic, an analgesic, an antiviral, an ion channel blocker and a free-radical antagonist.

* * * * *